US012594235B2

(12) United States Patent
Rees

(10) Patent No.: US 12,594,235 B2
(45) Date of Patent: Apr. 7, 2026

(54) INTRAORAL CLEANING TABLET

(71) Applicant: Dendisc Holdings Pty Ltd, Gold Coast Mail Centre (AU)

(72) Inventor: Frank Rees, Tweed Heads (AU)

( * ) Notice: Subject to any disclaimer, the term of this patent is extended or adjusted under 35 U.S.C. 154(b) by 0 days.

(21) Appl. No.: 19/339,250

(22) Filed: Sep. 24, 2025

(65) Prior Publication Data

US 2026/0021034 A1      Jan. 22, 2026

Related U.S. Application Data

(63) Continuation-in-part of application No. 18/072,437, filed on Nov. 30, 2022, now abandoned.

(51) Int. Cl.
*A61K 8/9789*      (2017.01)
*A61Q 11/00*      (2006.01)

(52) U.S. Cl.
CPC ............ *A61K 8/9789* (2017.08); *A61Q 11/00* (2013.01); *A61K 2800/92* (2013.01)

(58) Field of Classification Search
CPC . A23G 4/068; A23G 4/12; A23G 3/48; A61C 17/00; A61K 8/11; A61K 8/9789; A61K 8/0216; A61Q 11/00; A23V 2002/00
See application file for complete search history.

(56) References Cited

U.S. PATENT DOCUMENTS 2,812,256 A * 11/1957 Nerfin .................. A61K 9/0058
424/48

FOREIGN PATENT DOCUMENTS

CN          109105790 A  *  1/2019    ............. A23L 33/00
DE          102011084162 A1 *  4/2013    ............. A23L 27/12
WO      WO-2024003682 A1 *  1/2024    ............... A23G 4/10

* cited by examiner

*Primary Examiner* — Lezah Roberts
(74) *Attorney, Agent, or Firm* — Daniel Polk

(57)      ABSTRACT

The intraoral cleaning tablet has a chewable gum to stimulate saliva and a fibrous ingestible material in the form of dried apple peel. The dried apple peel embedded within the chewable gum in order to clean the teeth. The chewable gum is plastic-free and biodegradable, comprised of ingredients such as mastic or chicle.

6 Claims, No Drawings

INTRAORAL CLEANING TABLET

CROSS-REFERENCE TO RELATED APPLICATION

This application is a continuation of U.S. patent application Ser. No. 18/072,437, filed on Nov. 30, 2022, which is hereby incorporated by reference in its entirety.

BACKGROUND

1. Field of the Invention

The present invention relates to the dental industry and, more particularly to an intraoral cleaning tablet which is safe to ingest, and which can remove plaque and debris from the teeth, gums and the oral cavity without the use of water.

2. Description of Related Art

The most common way to clean teeth is with a toothbrush and toothpaste. However, it is not always convenient to use these items. Running water for rinsing the mouth is not always available.

Pfizer Inc. produces an oral care strip (sold under the Listerine trademark) which dissolves in the mouth and freshens the breath. However, these oral care strips do not clean the teeth.

Prior chewable toothpaste tablets can be used to create toothpaste in the mouth of the user when mixed with their saliva. However, a brush is required to remove debris and plaque from the teeth. A brush may not be available. Moreover, these chewable toothpaste tablets are not ingestible. Accordingly, if water is not available to rinse the mouth, then chewable toothpaste tablets are not practical.

Traditional chewing gums can be used to freshen the mouth, but they are not ingestible, or at least are not recommended for ingestion. Most chewing gums contain plastic, which is indigestible.

The object of the present invention is to provide an oral hygiene product which is safe to ingest, and which can remove plaque and debris from the teeth, gums and the oral cavity without the use of water.

SUMMARY OF THE INVENTION

According to the present invention, there is provided an intraoral cleaning tablet comprising:

(a) a chewable gum to stimulate saliva; and (b) a fibrous ingestible material;

wherein:

(i) that the fibrous ingestible material is dried apple peel embedded within the chewable gum in order to clean the teeth; and (ii) the chewable gum is plastic-free and biodegradable.

The term 'tablet' can include any substance to be put into the mouth, including gums, jubes or cubes of any shape. The tablets may be coated or uncoated.

The chewable gum may include mastic gum (*Pistacia lentiscus*), chicle, gum Arabic, gum acacia, Chios Mastic Tree gum resin, glycerol, or waxes (such as bee's wax, carnauba wax, Candelilla wax).

The tablet may include a lubricant, such as magnesium stearate (produced from palm oil), or a combination of other ingredients such as rice extract, rice hulls, gum arabic and sunflower oil.

Preferably, the fibrous material is freeze-dried before being embedded within the chewable gum. The fibrous material may be compressed and freeze-dried.

The chewable gum may contain additives, such as calcium including hydroxyapatite, calcium phosphate (mono basic, dibasic or tribasic), calcium glycero-phosphate, calcium citrate, calcium carbonate, calcium lactate. The chewable gum may contain other additives such as sodium bicarbonate, commiphora myrrha (myrrh) gum oleoresin powder, piper nigrum (black pepper) essential oil, Xylitol, or hydroxyapatite.

Preferably, the tablet also contains a gelatinous substance, such as agar. The gelatinous substance may contain agents for polishing, flavouring, breath freshening and/or desensitising the teeth. The gelatinous substance may also include a health supplement, such as zinc or fluoride. The gelatinous substance may include catalytic nanozyme to reduce plaque.

The breath freshening agent may be one or more essential oils, such as mint, spearmint, peppermint, eucalyptus, piper nigrum (black pepper) oil, citrus oils (such as lemon or orange), cloves, cinnamon, or ginger.

The tablet may include menthol as a cooling and flavouring agent.

According to another aspect of the present invention, there is provided a method of making an intraoral cleaning tablet comprising the steps of:

(a) collecting apple peel;

(b) drying the apple peel;

(c) blending the apple peel with other ingredients for the tablet to form a composition;

(d) compressing the composition; and (e) forming the composition into a tablet.

The method may also include a step of coating the tablet in a gum. The method may also include the step of freezing the dried apple peel.

Preferably, the fibrous ingestible material is organic and contains no pesticides or herbicides.

Any of the features described herein can be combined in any combination with any one or more of the other features described herein within the scope of the invention.

DETAILED DESCRIPTION OF THE INVENTION

The fibrous ingestible material in the form of apple peel, which is embedded within a chewable gum. The gum is preferably mastic gum but may also be chicle.

The tablet could be in the form of a hard tablet, or soft gum or jube.

The tablet can be coated or uncoated.

When the tablet is chewed, the apple peel removes the plaque and debris from the teeth, gums and oral cavity.

The apple peel is an organic material which is inherently flavoured. If the apple peel is swallowed, it would do no harm.

Chewing or sucking the tablet can help to remove plaque and stimulate saliva.

The tablet is moved around within the mouth by the tongue, cheeks and lips to clean all areas of the mouth and teeth.

The tablet contains additives, such as essential oils (including eucalyptus oil or peppermint oil). Peppermint oil is a popular essential oil used alone and in combination with other essential oils. Menthol is the main component of peppermint oil and is responsible for the noticeable cooling sensation.

The tablet contains calcium hydroxyapatite, which is useful for tooth health.

The tablet may include health supplements, such as zinc, fluoride, and Vitamin C, prebiotics, probiotics, postbiotics and herbal ingredients.

The tablet may also include catalytic nanozyme to reduce plaque.

The intraoral cleaning tablet is made by:

(a) collecting apple peel;

(b) drying the apple peel;

(c) blending the apple peel with other ingredients for the tablet to form a composition;

(d) compressing the composition; and (e) forming the composition into a tablet.

The method preferably includes the step of freezing the dried apple peel. The method may include a step of coating the tablet in a gum.

The present invention provides an oral hygiene product which is safe to ingest because it contains organic ingredients that are plastic-free and biodegradable, which can remove plaque and debris from the teeth, gums and the oral cavity without the use of water.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

In certain embodiments, the chewing gum composition comprises about 40-55% chicle gum base, 25-35% erythritol, 2-6% freeze dried apple peel, 2-6% fibre gum B, 2-6% fermented dried apple peel, 2-5% carnauba wax, 1-4% acetylated distarch adipate, 1-4% novelose resistant starch, 0.5-2% calcium carbonate, 0.5-2% magnesium stearate, 0.5-2% peppermint oil, 0.5-2% natural apple flavour, 0.1-1% natural peppermint flavour, 0.1-1% glycerol, 0.05-0.5% stevia, 0.01-0.2% vitamin E, and optionally up to 0.1% thaumatin and/or up to 0.1% citric acid.

In certain embodiments, the chewing gum composition described herein may be enclosed within an edible, prebiotic wrapper. The wrapper may take the form of a thin film, a sheet that fully wraps the gum, or a pouch or envelope that surrounds the gum piece in an air-tight manner. In another embodiment, the wrapper may form a pouch around the gum in a bag-like configuration, which may be either airtight or non-airtight, depending on the desired storage and functional properties. The wrapper not only serves as packaging but also provides an additional functional benefit by delivering prebiotic dietary fibers that support gut health. Suitable prebiotic materials for forming the edible wrapper include, but are not limited to, pullulan, inulin, fructooligosaccharides (FOS), galactooligosaccharides (GOS), resistant starch, pectin, arabinoxylans, beta-glucans, and gum arabic. These materials may be combined with edible film-forming agents such as hydroxypropyl methylcellulose (HPMC), methylcellulose, starch derivatives, or alginate to achieve desirable mechanical strength, flexibility, and dissolution properties.

The wrapper may be prepared as a thin film using solvent casting, extrusion, or compression molding techniques, and may optionally incorporate plasticizers (e.g., glycerol, sorbitol, or maltitol) to improve flexibility. Flavoring agents (such as natural fruit extracts, essential oils, or sweeteners like stevia) and colorants (such as plant-based pigments) may also be included to enhance palatability and consumer appeal. In some embodiments, the wrapper is designed to dissolve rapidly in the oral cavity, releasing prebiotic fibers concurrently with mastication of the gum.

In one embodiment, the chewing gum composition is enclosed in an edible, prebiotic wrapper formulated from approximately 40% w/w inulin, 40% w/w pullulan, 15% w/w glycerol, 3% w/w natural apple extract, and 2% w/w stevia. The inulin and pullulan are dissolved in deionized water at 60° C. with continuous stirring until a homogeneous solution is achieved. Glycerol is then added as a plasticizer to impart flexibility to the film, after which natural apple extract and stevia are incorporated as flavoring and sweetening agents. The solution is cast onto a sterile, flat glass or stainless steel surface to form a uniform layer approximately 0.2 mm thick. The film is dried at 40° C. under controlled humidity (30-40% RH) for 12 hours until the moisture content is below 10%. Once dried, the film is cut into rectangular sheets sized appropriately to wrap individual gum pieces. The resulting wrapper is flexible, transparent, and capable of tightly enclosing the gum without tearing. Upon oral dissolution, the wrapper releases inulin as a prebiotic fiber, along with flavor and sweetness, thereby enhancing the functional and sensory profile of the gum product.

What is claimed is:

1. A chewing gum composition comprising at least 40% chicle gum base, at least 25% erythritol, at least 2% freeze dried apple peel, at least 2% gum acacia, at least 2% fermented dried apple peel, at least 2% carnauba wax, at least 1% acetylated distarch adipate, at least 1% resistant starch, at least 0.5% calcium carbonate, at least 0.5% magnesium stearate, at least 0.5% peppermint oil, at least 0.5% natural apple flavour, at least 0.1% natural peppermint flavour, at least 0.1% glycerol, at least 0.05% stevia, and at least 0.01% vitamin E, wherein the percentages are expressed as weight percent of the total chewing gum composition.

2. The chewing gum composition of claim 1, wherein the chicle gum base is present in the range of about 40-55% by weight of the total composition.

3. The chewing gum composition of claim 2, wherein the erythritol is present in the range of about 25-35% by weight of the total composition.

4. The chewing gum composition of claim 3, wherein the freeze dried apple peel, fibre gum B, and fermented dried apple peel are each present in the range of about 2-6% by weight of the total composition.

5. The chewing gum composition of claim 4, wherein the composition further comprises about 0.01-0.2% vitamin E, about 0.05-0.5% stevia, and optionally up to 0.1% thaumatin and/or up to 0.1% citric acid.

6. The chewing gum composition of claim 5, wherein the composition is enclosed within an edible, prebiotic wrapper comprising inulin, pullulan, glycerol, natural apple extract, and stevia.

\* \* \* \* \*